United States Patent
Kim et al.

(10) Patent No.: US 9,896,701 B2
(45) Date of Patent: Feb. 20, 2018

(54) METHOD FOR PRODUCING 1,3-PROPANEDIOL USING MICROORGANISM VARIANT WITH DELETION OF 2,3-BUTANEDIOL SYNTHETIC GENE

(71) Applicant: KOREA RESEARCH INSTITUTE OF BIOSCIENCE AND BIOTECHNOLOGY, Daejeon (KR)

(72) Inventors: Chul Ho Kim, Daejeon (KR); Jeong-Woo Seo, Daejeon (KR); Sun-Yeon Heo, Daejeon (KR); Sung Mok Lee, Busan (KR); Jang Min Park, Daejeon (KR); Baek Rock Oh, Daejeon (KR); You Ree Jung, Daejeon (KR)

(73) Assignee: KOREA RESEARCH INSTITUTE OF BIOSCIENCE AND BIOTECHNOLOGY, Daejeon (KR)

( * ) Notice: Subject to any disclaimer, the term of this patent is extended or adjusted under 35 U.S.C. 154(b) by 23 days.

(21) Appl. No.: 15/120,516

(22) PCT Filed: Feb. 16, 2015

(86) PCT No.: PCT/KR2015/001533
§ 371 (c)(1),
(2) Date: Aug. 20, 2016

(87) PCT Pub. No.: WO2015/126112
PCT Pub. Date: Aug. 27, 2015

(65) Prior Publication Data
US 2017/0016032 A1  Jan. 19, 2017

(30) Foreign Application Priority Data
Feb. 24, 2014 (KR) .................. 10-2014-0021351

(51) Int. Cl.
*C12P 7/18* (2006.01)
*C12N 1/00* (2006.01)
(Continued)

(52) U.S. Cl.
CPC .................. *C12P 7/18* (2013.01); *C12N 1/00* (2013.01); *C12N 1/20* (2013.01); *C12N 9/0006* (2013.01);
(Continued)

(58) Field of Classification Search
None
See application file for complete search history.

(56) References Cited

U.S. PATENT DOCUMENTS

| 6,136,576 A | 10/2000 | Diaz-Torres et al. |
| 2007/0148749 A1* | 6/2007 | Yasuda ................. C12N 15/52 435/158 |
| 2010/0196977 A1* | 8/2010 | Chotani .................. C12N 9/88 435/158 |

FOREIGN PATENT DOCUMENTS

| EP | 2407544 A1 | 1/2012 |
| KR | 10-2013-0025701 A | 3/2013 |

OTHER PUBLICATIONS

English Translation of KR 10-2013-0025701, published Mar. 12, 2013.*

(Continued)

*Primary Examiner* — Richard Ekstrom
(74) *Attorney, Agent, or Firm* — Hultquist, PLLC; Steven J. Hultquist (57) ABSTRACT

The present invention relates to a method for producing 1,3-propanediol using a mutant microorganism lacking a 2,3-butanediol synthetic gene, and more particularly to a mutant microorganism wherein a gene encoding lactate dehydrogenase and a gene encoding an enzyme which is (Continued)

involved in 2,3-butanediol synthesis are deleted in a microorganism having the ability to produce 1,3-propanediol from glycerol and wherein a gene encoding pyruvate decarboxylase and a gene encoding aldehyde dehydrogenase are introduced or amplified, and to a method of promoting the production of 1,3-propanediol while inhibiting the production of 2,3-butanediol by using the mutant microorganism. The use of the glycerol-fermenting mutant microorganism according to the present invention can significantly increase the production of 1,3-propanediol while minimizing the production of 2,3-butanediol.

7 Claims, 8 Drawing Sheets (51) Int. Cl.
    *C12N 1/20*     (2006.01)
    *C12N 9/04*     (2006.01)
    *C12N 9/02*     (2006.01)
    *C12N 9/10*     (2006.01)
    *C12N 9/00*     (2006.01)
    *C12N 9/88*     (2006.01)

(52) U.S. Cl.
    CPC ......... *C12N 9/0008* (2013.01); *C12N 9/1022* (2013.01); *C12N 9/88* (2013.01); *C12N 9/93* (2013.01); *C12Y 202/01006* (2013.01); *C12Y 401/01001* (2013.01)

(56) References Cited

OTHER PUBLICATIONS

Lee et al., "Enhancement of 1,3-propanediol production by expression of pyruvate decarboxyalse and aldehyde dehydrogenase from Zymomonas mobilis in the acetolactate-synthase-deficient mutant of Klebsiella pneumoniae", Journal of Industrial Microbiology and Biotechnology, vol. 41, pp. 1259-1266, 2014 (published online May 20, 2014).*

Kumar et al., "Simultaneous production of 3-hydroxypropionic acid and 1,3-propanediol from glycerol using resting cells of the lactate dehydrogenase-deficient recombinant Klebsiella pneumoniae overexpressing an aldehyde dehydrogenase", Bioresource Technology, vol. 135, pp. 555-563, 2013 (published online Nov. 15, 2012).*

Da Silva, G., et al., "Glycerol: A promising and Abundant Carbon Source for Industrial Microbiology", "Biotechnology Advances", 2009, pp. 30-39, vol. 27.

Johnson, D., et al., "The Glycerin Glut: Options for the Value-Added Conversion of Crude Glycerol Resulting from Biodiesel Production", "Environmental Progress", Oct. 1, 2007, pp. 338-348, vol. 26, No. 4.

Oh, B., et al., "Optimization of Culture Conditions for 1,3-Propanediol Production from Glycerol Using a Mutant Strain of Klebsiella pneumoniae", "Applied Biochemistry and Biotechnology", 2012, pp. 127-137, vol. 166.

* cited by examiner

A: Δ ldhA (2.0 vvm)

B: Δ (ldhA als) (2.0 vvm)

C: Δ (ldhA als)/pPdc-aldB (2.0 vvm)

A: Δ (*ldhA als*)/pPdc-aldB (0.5 vvm)

B: Δ (*ldhA als*)/pPdc-aldB (3.0 vvm)

SEQUENCE LISTING

<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
acccgcaata attcgagctg                                           20

<210> SEQ ID NO 2
<211> LENGTH: 49
<212> TYPE: DNA
<213> ORGANISM: Artificial Sequence

```
<220> FEATURE:
<223> OTHER INFORMATION: primer

<400> SEQUENCE: 2
gagcgctgta ccgctttgta gttaacgcga taggtttaaa gacgctcag         49

<210> SEQ ID NO 3
<211> LENGTH: 49
<212> TYPE: DNA
<213> ORGANISM: Artificial Sequence
<220> FEATURE:
<223> OTHER INFORMATION: primer

<400> SEQUENCE: 3
ctgagcgtct ttaaacctat cgcgttaact acaaagcggt acagcgctc         49

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
agagagcgag cgcgaataaa                                         20

<210> SEQ ID NO 5
<211> LENGTH: 32
<212> TYPE: DNA
<213> ORGANISM: Artificial Sequence
<220> FEATURE:
<223> OTHER INFORMATION: primer

<400> SEQUENCE: 5
agatctatgg cttcttcaac ttttatatt cc                            32

<210> SEQ ID NO 6
<211> LENGTH: 35
<212> TYPE: DNA
<213> ORGANISM: Artificial Sequence
<220> FEATURE:
<223> OTHER INFORMATION: primer

<400> SEQUENCE: 6
ctcgagtcta gattagaaag cgctcaggaa gagtt                        35

<210> SEQ ID NO 7
<211> LENGTH: 35
<212> TYPE: DNA
<213> ORGANISM: Artificial Sequence
<220> FEATURE:
<223> OTHER INFORMATION: primer

<400> SEQUENCE: 7
tctagaatga gttatactgt cggtacctat ttagc                        35

<210> SEQ ID NO 8
<211> LENGTH: 38
<212> TYPE: DNA
<213> ORGANISM: Artificial Sequence
<220> FEATURE:
<223> OTHER INFORMATION: primer

<400> SEQUENCE: 8
ctcgagctgc agctagagga gcttgttaac aggcttac                     38
```

METHOD FOR PRODUCING 1,3-PROPANEDIOL USING MICROORGANISM VARIANT WITH DELETION OF 2,3-BUTANEDIOL SYNTHETIC GENE

CROSS-REFERENCE TO RELATED APPLICATIONS

This application is a U.S. national phase under the provisions of 35 U.S.C. § 371 of International Patent Application No. PCT/KR15/01533 filed Feb. 16, 2015, which in turn claims the priority of Korean Patent Application No. 10-2014-0021351 filed Feb. 24, 2014. The disclosures of such international patent application and Korean priority patent application are hereby incorporated herein by reference in their respective entireties, for all purposes.

GOVERNMENTAL SUPPORT OF INVENTION

This application is financially supported by the 2016 Commercialization Project for Promising Technologies of the government of the Republic of Korea.

TECHNICAL FIELD

The present invention relates to a method for producing 1,3-propanediol using a mutant microorganism lacking a 2,3-butanediol synthetic gene, and more particularly to a mutant microorganism wherein a gene encoding lactate dehydrogenase and a gene encoding an enzyme which is involved in 2,3-butanediol synthesis are deleted in a microorganism having the ability to produce 1,3-propanediol from glycerol and wherein a gene encoding pyruvate decarboxylase and a gene encoding aldehyde dehydrogenase are introduced or amplified, and to a method of promoting the production of 1,3-propanediol while inhibiting the production of 2,3-butanediol by using the mutant microorganism.

BACKGROUND ART

In current biodiesel production processes, crude glycerol is produced as a major by-product in an amount corresponding to about 10% (w/w) of the total amount of products (Johnson and Taconi, Environ Prog, 26:338, 2007). Such crude glycerol has an impact on the market price of glycerol and is also considered a cause of environmental problems because it is not permitted to discharge such crude glycerol directly to the environment (da Silva et al. Biotechnol Adv, 27:30, 2009). For these reasons, methods have been developed in order to convert inexpensive crude glycerol to fuels and industrially valuable substances, including physiologically active substances.

Glycerol can be converted to a variety of chemical raw materials by microbial fermentation, and a typical example of such chemical raw materials is 1,3-propanediol. 1,3-propanediol can be used as a raw material for synthesizing polyester, polyether or polyurethanes, and is used in various applications, including textiles such as highly functional clothes, carpets or vehicle textiles, and plastic films. In particular, polytrimethylene terephtalate (PTT) that is produced by polymerization of 1,3-propanediol and terephthalic acid has excellent physical properties and a melting point of 228° C., which is lower than that of polyethylene terephtalate (PET), and thus the actual usefulness thereof is higher. Accordingly, PTT is attracting attention as a next-generation fiber material. Furthermore, plastic and polymer products made using 1,3-propanediol as a monomer shows better optical stability than products made using butanediol or ethylene glycol. In addition, 1,3-propanediol can be used as a polyglycol-type lubricant and a solvent, and thus is evaluated to have a higher commercial value than glycerol.

Figure 1:
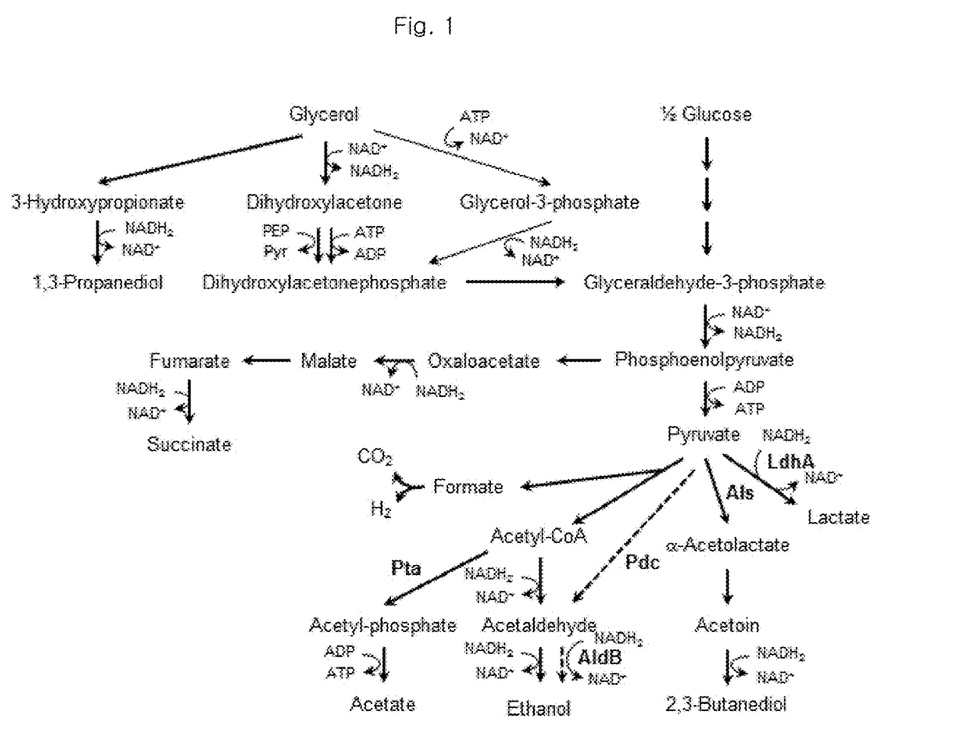
FIG. 1 shows the glycerol metabolic pathway in *Klebsiella pneumoniae*.

Up to date, a glycerol-fermenting microorganism reported to show the highest production of 1,3-propanediol is *Klebsiella pneumoniae*, and studies on the glycerol fermentation metabolic pathways of *Klebsiella pneumoniae* have been actively conducted (FIG. 1). *Klebsiella pneumoniae* produces 1,3-propanediol by reduction of glycerol and, at the same time, produces large amounts of competitive metabolites such as 2,3-butanediol by oxidation of glycerol. Thus, attempts have been actively made to promote the production of 1,3-propanediol by inhibiting the production of major competitive metabolites *in Klebsiella pneumoniae*. It was typically found that the production of 1,3-propanediol can be increased by inhibiting the production of lactic acid in a mutant wherein lactate dehydrogenase is deleted (Oh et al. Appl Biochem Biotechnol 166:127-137, 2012). Inhibition of the production of competitive metabolites in *Klebsiella pneumoniae* is very advantageous not only for promotion of the production of 1,3-propanediol, but also for efficient purification of 1,3-propanediol. In particular, because 2,3-butanediol that is a major competitive metabolite has physicochemical properties very similar to those of 1,3-propanediol, it acts as a big obstacle in purification of 1,3-propanediol when it is present in a mixture with 1,3-propanediol. In recent years, several research groups have developed mutants wherein a 2,3-butandiol synthetic pathway is deleted in *Klebsiella pneumonia* (Oh et al. Appl Biochem Biotechnol 166:127-137, 2012). However, it was shown that the production of 1,3-propanediol in the mutant lacking the 2,3-butandiol synthetic pathway decreased while the fermentative metabolism of glycerol and the growth of cells were reduced, although the reason therefor has not yet been clear.

Accordingly, the present inventors have made extensive efforts to develop a method of increasing the production of 1,3-propanediol in a mutant lacking the 2,3-butanediol synthetic pathway, and as a result, have found that, when a mutant strain expressing the pyruvate decarboxylase and aldehyde dehydrogenase genes is used, the production yield of 1,3-propanediol can be increased while the production of 2,3-butanediol is inhibited, thereby completing the present invention.

DISCLOSURE OF INVENTION

Technical Problem

It is an object of the present invention to provide a mutant microorganism which produces 1,3-propanediol in high yield while inhibiting the production of 2,3-butanediol.

Another object of the present invention is to provide a method of producing 1,3-proppanediol in high yield while inhibiting the production of 2,3-butanediol by culturing a glycerol-fermenting mutant microorganism.

Technical Solution

To achieve the above object, the present invention provides a mutant microorganism wherein a gene encoding lactate dehydrogenase and a gene encoding an enzyme which is involved in 2,3-butanediol synthesis are deleted in a microorganism having the ability to produce 1,3-propanediol from glycerol and wherein a gene encoding pyruvate decarboxylase and a gene encoding aldehyde dehydrogenase are introduced or amplified.

The present invention also provides a method for producing 1,3-propanediol, comprising the steps of: (a) culturing the mutant (Δ(ldhA als)/pPdc-AldB) in a glycerol-containing medium to produce 1,3-propanediol; and (b) recovering the produced 1,3-propanediol.

BEST MODE FOR CARRYING OUT THE INVENTION

Unless defined otherwise, all technical and scientific terms used herein have the same meaning as commonly understood by one of ordinary skill in the art to which the invention pertains. Generally, the nomenclature used herein and the experiment methods, which will be described below, are those well known and commonly employed in the art.

In one aspect, the present invention is directed to a mutant microorganism wherein a gene encoding lactate dehydrogenase and a gene encoding an enzyme which is involved in 2,3-butanediol synthesis are deleted in a microorganism having the ability to produce 1,3-propanediol from glycerol and wherein a gene encoding pyruvate decarboxylase and a gene encoding aldehyde dehydrogenase are introduced or amplified.

As used herein, "deletion" of a gene means a state in which the gene is deleted from the chromosome or a plasmid so that a protein encoded by the gene cannot be produced.

In the present invention, the microorganism having the ability to produce 1,3-propanediol from glycerol may be *Klebsiella pneumoniae*, and is preferably one wherein a gene encoding lactate dehydrogenase is deleted.

Figure 2:
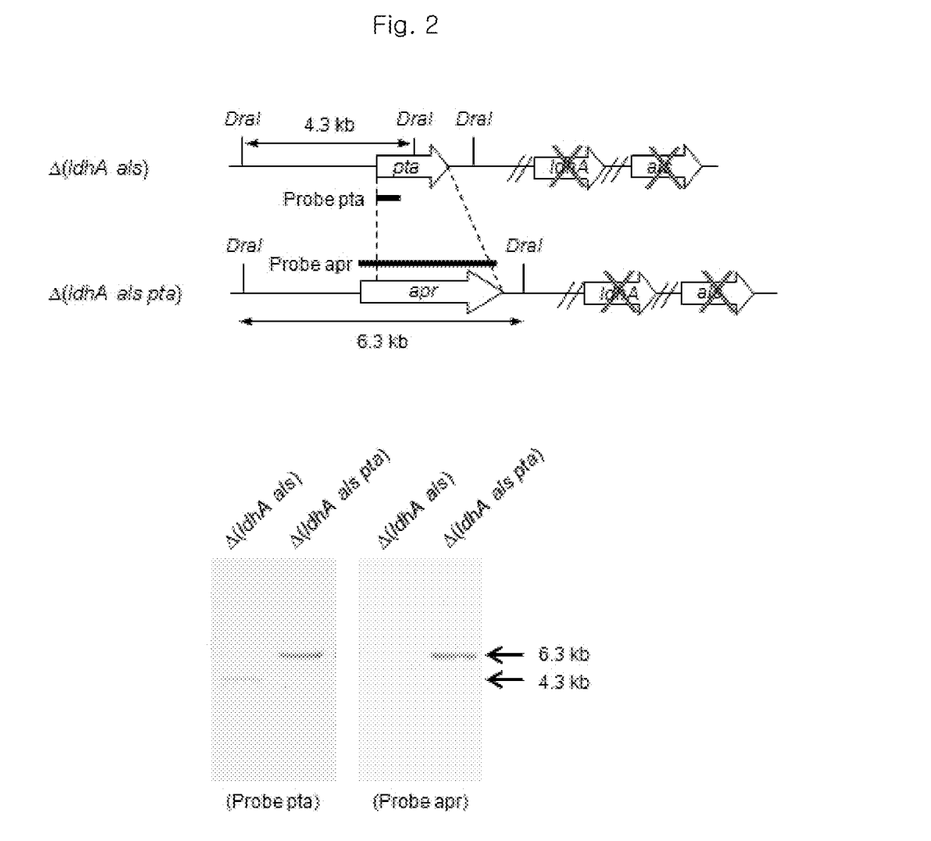
FIG. 2 shows a process for constructing a *Klebsiella pneumoniae* Δ(ldhA als pta) mutant.

In an example of the present invention, the mutant Δ(ldhA als pta) was constructed either by substituting the 2,3-butanediol synthetic gene present on the *Klebsiella pneumoniae* (ΔldhA)) chromosome with the antibiotic apramycin-resistant gene to remove the 2,3-butanediol synthetic gene from the chromosome to thereby delete the acetolactate synthase gene (als) or by deleting the phosphate acetyltransferase gene (pta) in order to examine the effect of an increase in acetic acid production on the production of 1,3-propanediol (FIG. 2 and Table 2).

Figure 4:
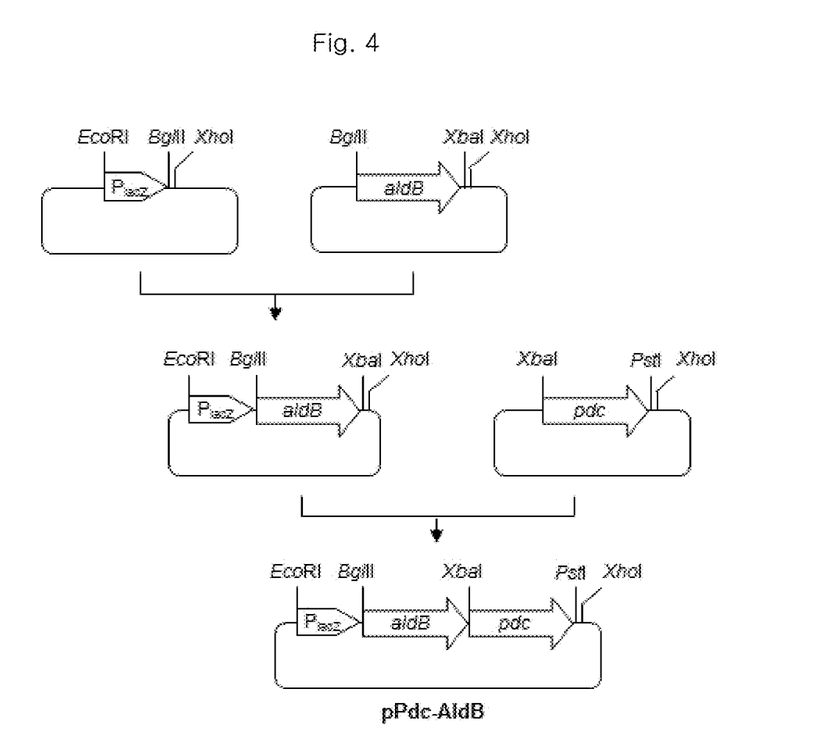
FIG. 4 shows a process for constructing a pyruvate decarboxylase/aldehyde dehydrogenase expression vector.
Figure 5:
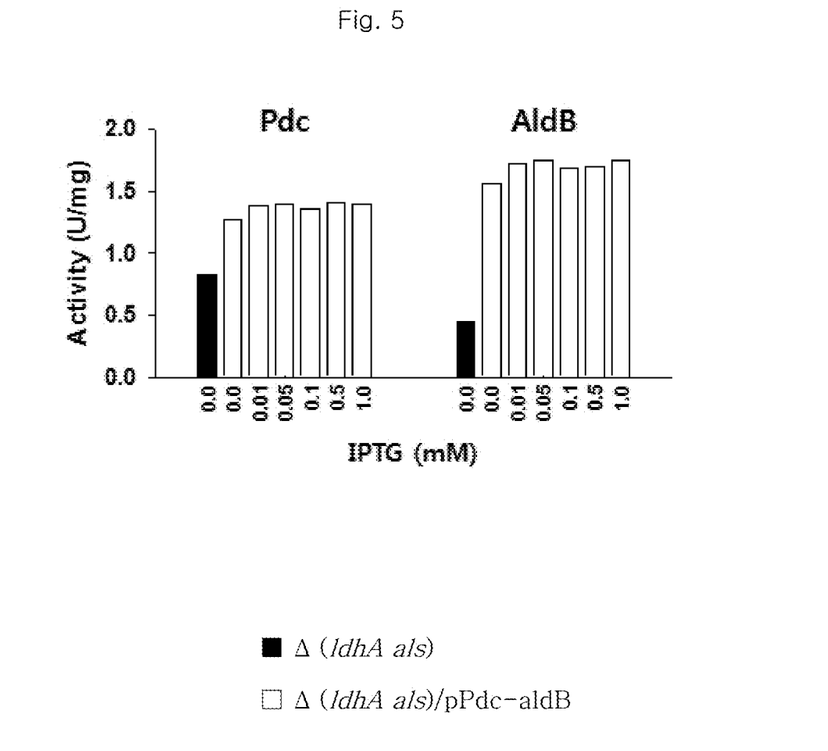
FIG. 5 shows the results of examining the enzymatic activity of the *Klebsiella pneumoniae* mutant Δ(ldhA als)/pPdc-AldB.

In another example of the present invention, the recombinant strain Δ(ldhA als)/pPdc-AldB was prepared by introducing the pyruvate decarboxylase gene (pdc) and the aldehyde dehydrogenase gene (aldB), which promote pyruvate-to-ethanol conversion, into the mutant Δ(ldhA als) lacking the 2,3-butanediol synthetic pathway, and the activities of Pdc and AldB enzymes in the mutant Δ(ldhA als)/pPdc-AldB were examined. As a result, it could be seen that the activities of the enzymes increased (FIGS. 4 and 5 and Table 3).

In another aspect, the present invention is directed to a method for producing 1,3-propanediol, comprising the steps of: (a) culturing the mutant (Δ(ldhA als)/pPdc-AldB) in a glycerol-containing medium to produce 1,3-propanediol; and (b) recovering the produced 1,3-propanediol.

In the present invention, the mutant Δ(ldhA als)/pPdc-AldB which is cultured to produce 1,3-propanediol may not express the 2,3-butanediol synthetic gene (als) and may express the Pdc and AldB genes, which promote pyruvate-to-ethanol conversion, in the glycerol metabolic process.

In the present invention, the gene encoding pyruvate decarboxylase may be pdc derived from a mutant microorganism, preferably *Zymomonas mobilis*, which has pyruvate decarboxylase activity. In addition, the gene encoding aldehyde dehydrogenase may be aldB derived from a mutant microorganism, preferably *Zymomonas mobilis*, which has pyruvate decarboxylase activity.

In the present invention, it was found that, in the mutant Δ(ldhA als) obtained by deleting the acetolactate synthase (als) gene from a *K. pneumonia* strain (ATCC 20071), 2,3-butanediol was not produced, but the production of most metabolites, including 1,3-propanediol, decreased, while glycerol metabolism and cell growth decreased 44% and 62%, respectively (Table 1).

Figure 6:
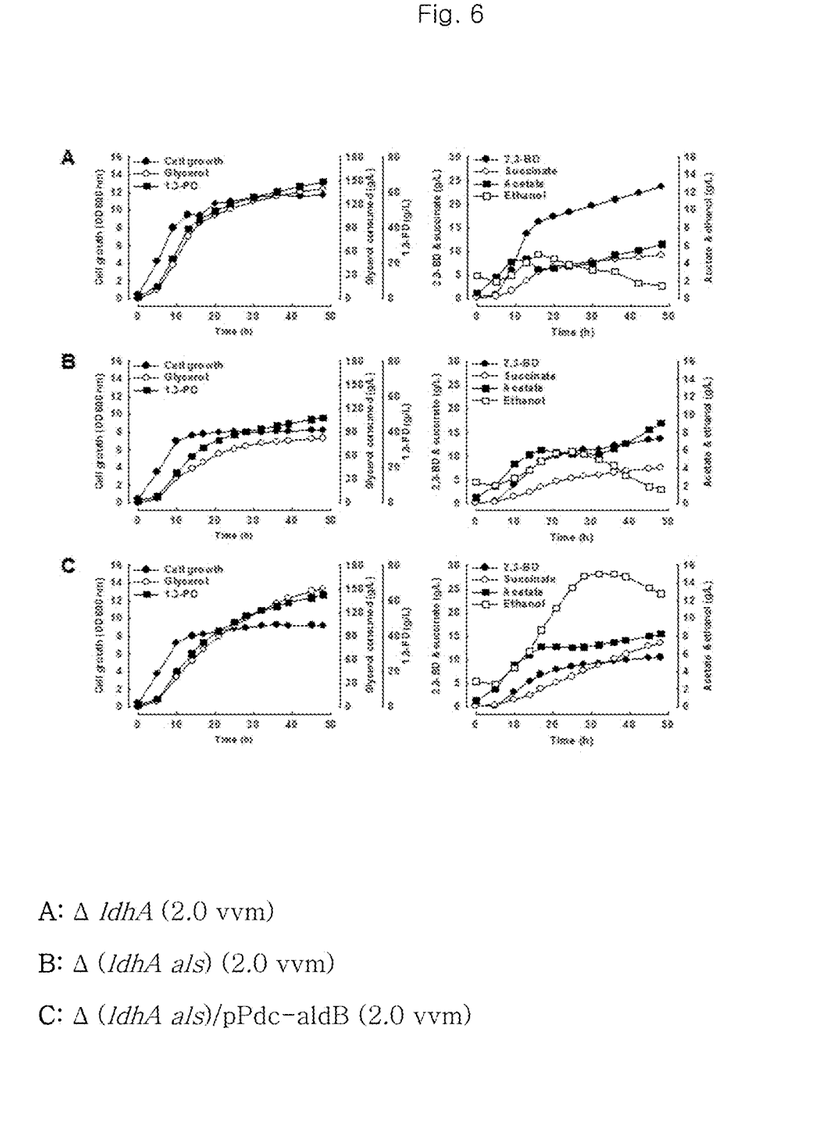
FIG. 6 shows the results of fed-batch culture processes for glycerol fermentation by the *Klebsiella pneumoniae* mutants ΔldhA, Δ(ldhA als) and Δ(ldhA als)/pPdc-AldB. A: ΔldhA (2.0 vvm); B: Δ(ldhA als) (2.0 vvm); and C: Δ(ldhA als)/pPdc-aldB (2.0 vvm).

In addition, it was shown that, in the mutant Δ(ldhA als pta) obtained by additionally deleting phosphate acetyltransferase from the mutant Δ(ldhA als), the production of acetic acid increased 37%, unlike the lactic acid mutant ΔldhA that is a control strain, and glycerol fermentative metabolism and cell growth were similar to those in the mutant Δ(ldhA als) and lower than those in the control strain, and also the production of most metabolites, including 1,3-propanediol, decreased (FIG. 6 and Table 1).

In another example of the present invention, in order to analyze the fermentative metabolism characteristics of glycerol in the mutant Δ(ldhA als)/pPdc-AldB, the mutant was cultured in a medium containing glycerol as a single carbon source, and as a result, it could be seen that the mutant showed cell growth and glycerol metabolism characteristics, which were almost similar to those of the control strain and increased 52% and 57% compared to those of the mutants Δ(ldhA als pta) and Δ(ldhA als), respectively, and the production of 2,3-butanediol in the mutant Δ(ldhA als)/pPdc-AldB was as low as 0.12 g/L (Table 1).

Figure 7:
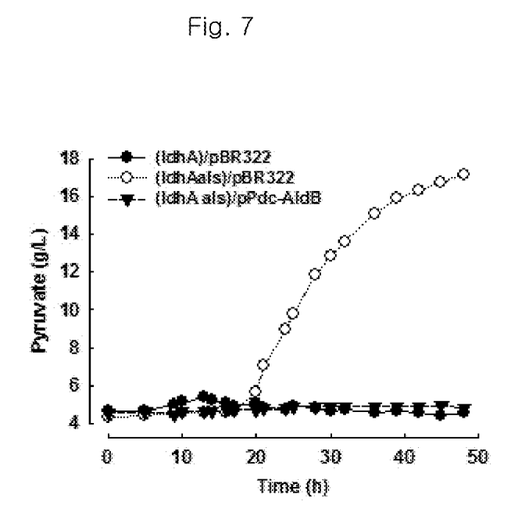
FIG. 7 shows the results of analyzing pyruvate in a fed-batch culture process for glycerol fermentation in a *Klebsiella pneumoniae* mutant.

In addition, it was found that the concentration of pyruvate during growth of the mutant Δ(ldhA als) greatly increased, but the concentration of pyruvate in the mutant Δ(ldhA als)/pPdc-AldB decreased to a level similar to that in the mutant ΔldhA (FIG. 7).

In still another example of the present invention, in order to analyze the fermentative metabolism characteristics of glycerol in the mutant Δ(ldhA als)/pPdc-AldB, the mutant was fed-batch cultured in a medium containing glycerol as a single carbon source. As a result, it was shown that the mutant showed cell growth and glycerol metabolism characteristics almost similar to those of the control strain, and the production of 1,3-propanediol in the mutant was 63.3 g/L, which is similar to that of the control strain (65.9 g/L), but the production of 2,3-burtanediol in the mutant was 76% lower than that in the mutant Δ(ldhA als), indicating that the concentration of 2,3-butanediol relative to that of 1,3-propanediol is 14% (mol/mol) which is the lowest value (FIG. 6 and Table 4).

In still another example of the present invention, the effect of the amount of air injection on the fed-batch culture of the mutant Δ(ldhA als)/pPdc-AldB was examined, and as a result, it was shown that, as the amount of air injected increased from 0.5 vvm to 2.0 vvm and 3.0 vvm, the production of 1,3-propanediol increased to 63.3 g/L (28%) and 68.2 g/L (38%). However, the production of 2,3-butanediol also increased from 7.6 g/L to 10.5 g/L and 12.0 g/L, indicating that the ratio of 2,3-butanediol to 1,3-butanediol was maintained at a similar level (Table 5).

EXAMPLES

Hereinafter, the present invention will be described in further detail with reference to examples. It will be obvious to a person having ordinary skill in the art that these examples are illustrative purposes only and are not to be construed to limit the scope of the present invention. Thus, the substantial scope of the present invention will be defined by the appended claims and equivalents thereof.

Example 1

Metabolite Productivity of *Klebsiella pneumoniae* Mutant Δ(ldhA als pta)

Using CuΔldhA, which showed high 1,3-propanediol productivity through strain improvement and culture processes, as a base strain, acetolactate synthase (als) gene which is involved in 2,3-butanediol production was removed from the chromosome by substitution with an antibiotic apramycin-resistant gene. For substitution with the apramycin-resistant gene, the ard up region and down region were amplified by PCR to about 600 by and ligated to each other, and then apramycin-resistant gene was inserted therein. The prepared cassette was introduced into the CuΔldhA strain which was then cultured in an apramycin-containing medium. The colonies isolated from the medium were subjected to PCR and Southern hybridization, and as a result, it was found that homologous recombination accurately occurred. Finally, a mutant strain lacking the als gene was constructed (FIG. 2).

In addition, in order to prevent acetic acid production that is a competitive metabolic pathway and to increase the production of 1,3-propanediol, the phosphate acetyltransferase (pta) gene that is involved in acetic acid production in the CuΔldhAΔals strain constructed as described above was removed from the chromosome by substitution with an antibiotic apramycin-resistant gene. For substitution with the apramycin-resistant gene, the ard up region and down region were amplified by PCR to about 300 by and ligated to each other, and then the apramycin-resistant gene was inserted therein. The prepared cassette was introduced into the CuΔldhAΔals strain which was then cultured in an apramycin-containing medium. The colonies isolated from the medium were subjected to PCR and Southern hybridization, and as a result, it was shown that homologous recombination accurately occurred. Finally, a mutant strain lacking the pta gene was constructed (FIG. 2 and Table 2).

For flask culture, the mutant strain was cultured in a 250 mL flask using crude glycerol (about 80%) as a carbon source, and changes in 1,3-propanediol production and metabolites were examined. The strain cultured in the solid medium was scratched with a loop, and the strain was inoculated in 20 mL of LB medium and cultured at 37° C. and 200 rpm for 10-12 hours. The strain cultured in the LB medium was inoculated in 100 mM of germ medium (10.7 g/L K2HPO4, 5.24 g/L KH2PO4 에 50 g/L crude glycerol, 2 g/L (NH4)2SO4, 0.2 g/L Mg504, 0.002 g/L CaCl2.2H2O, 1 g/L yeastextract, 1 ml of iron solution (5 g/L FeSO4.7H2O, 4 ml HCl (37%,w/v), 1 ml of trace element solution (70 mg/L ZnCl2, 100 mg/L MnCl2.4H2O, 60 mg/L H3BO3, 200 mg/L CoCl2.4H2O, 20 mg/L CuCl2.2H2O, 25 mg/L NiCl2.6H2O, 35 mg/L Na2MoO4.2H2O, 4 ml HCl (37%, w/v))]) in an amount corresponding to 2.5% of the culture volume and was cultured at 37° C. and 200 rpm. During the culture process, a sample was collected at 12-hour intervals, and metabolites in the sample were analyzed by HPLC.

In this Example, a total of four strains (ΔldhA, Δ(ldhA als), Δ(ldhA als pta), and Δ(ldhA als)/pPdc-aldB) were used and cultured in media containing 10 μg/mL of tetracycline and 0.5 mM of IPTG (Table 1).

A mutant strain lacking the acetolactate synthase gene (als) of the *K. pneumoniae* strain (ATCC 20071) was constructed and cultured in a glycerol-containing medium. As a result, it was shown that 2,3-butanediol was not produced in the mutant, but the production of most metabolites, including 1,3-propanediol, decreased while glycerol metabolism and cell growth decreased (Table 1).

Figure 3:
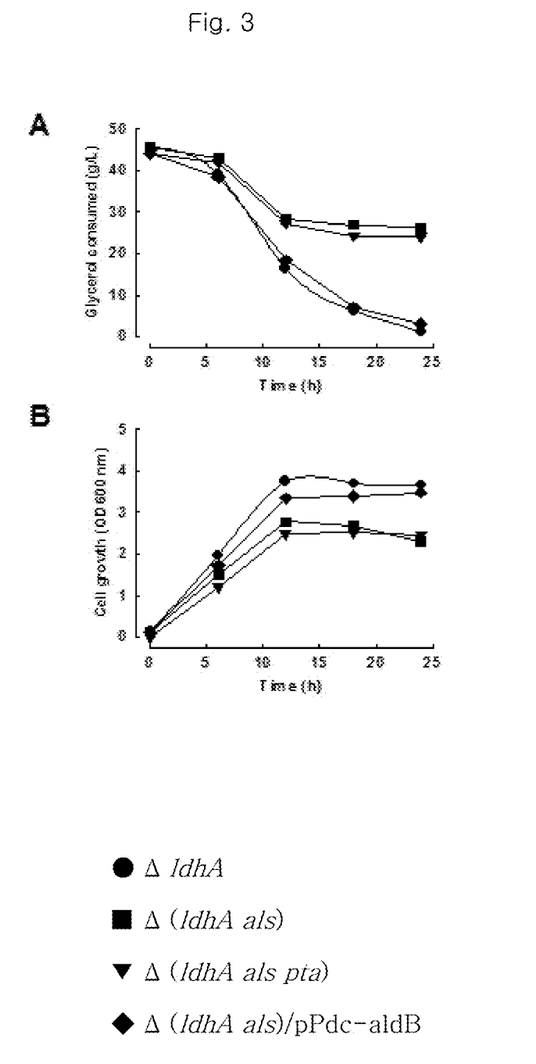
FIG. 3 shows the results of examining glycerol metabolism and cell growth in *Klebsiella pneumoniae* mutants (ΔldhA, Δ(ldhA als), Δ(ldhA als pta), and Δ(ldhA als)/pPdc-AldB).

Specifically, it was shown that the production of acetic acid in the mutant Δ(ldhA als) greatly increased, unlike that in the lactic acid mutant ΔldhA that is a parent strain. Thus, in order to examine the effect of an increase in acetic acid production in the mutant Δ(ldhA als), the mutant Δ(ldhA als pta) lacking phosphate acetyltransferase (Pta) was constructed (FIG. 2), and the fermentative metabolism characteristics of glycerol in the mutant were analyzed. As shown in Table 1 below, the production of acetic acid in the mutant Δ(ldhA als pta) decreased, but glycerol fermentative metabolism and cell growth were low and the production of 1,3-propanediol was not restored (FIG. 3).

TABLE 1

Fed-batch culture for glycerol fermentation in *Klebsiella pneumoniae* mutant

|  | ΔldhA | Δ(ldhA als) | Δ(ldhA als pta) | Δ(ldhA als)/ pPdc-AldB |
|---|---|---|---|---|
| Glycerol consumed (g/L) | 44.65 | 19.48 | 19.82 | 40.96 |
| Cell growth (OD600) | 3.67 | 2.30 | 2.52 | 3.48 |
| 1,3-Propanediol (g/L) | 17.46 | 9.05 | 9.38 | 14.26 |
| 2,3-Butanediol (g/L) | 5.38 | 0 | 0 | 0.12 |
| Lactate (g/L) | 0 | 0 | 0 | 0 |
| Succinate (g/L) | 1.75 | 0.74 | 1.08 | 1.79 |
| Acetate (g/L) | 1.49 | 4.09 | 2.05 | 2.14 |
| Ethanol (g/L) | 6.33 | 2.60 | 1.43 | 15.11 |

TABLE 2

Primer sequences used in construction of
Klebsiella pneumoniae mutant Δ (ldhA als pta)

| Primer | | Sequence |
|---|---|---|
| pta-up | SEQ ID NO. 1 | F:5'-acccgcaataattcgagctg-3' |
| | SEQ ID NO. 2 | R:5'-gagcgctgtaccgctttgta*GTTAAC*gcgataggtttaaagacgctcag-3' |
| pta-down | SEQ ID NO. 3 | F:5'-ctgagcgtctttaaacctatcgc*GTTAAC*tacaaagcggtacagcgctc-3' |
| | SEQ ID NO. 4 | R:5'-agagagcgagcgcgaataaa-3' |

Example 2

Metabolite Productivity of Klebsiella pneumoniae Mutant Δ(ldhA als)/pPdc-aldB In the case of the strain obtained by removing acetolactate synthase (als) and acetolactate decarboxylase (aldB), which are involved in 2,3-butanediol, from the chromosome of *K. pneumoniae* cuΔldhA, it could be seen that the production of 2,3-butanediol which interferes with the isolation and purification of 1,3-propanediol could be greatly reduced, but the production of 1,3-propanediol also greatly decreased. It was thought that one of the reasons why the production of 1,3-propanediol greatly decreases as described above is because of the accumulation of pyruvate in the metabolic process. Based on this thinking, in order to introduce an ethanol synthetic pathway that consumes pyruvate to increase cell growth rate and glycerol growth rate to thereby increase the production of 1,3-propanediol, a biosynthetic pathway that is involved in ethanol production was introduced into the cuΔldhAΔals strain.

From the ethanol-producing strain *Zymomonas mobilis* ZM4, pyruvate decarboxylase (pdc) and aldehyde dehydrogenase (aldB) which are involved in ethanol production were obtained by PCR amplification. The obtained genes were cloned into a pGEM-T easy vector, and then sequenced to confirm the accuracy of the amplified DNAs. The sequenced pdc and aldB genes were digested with bglII-XhoI or XbaI-XhoI, and then inserted downstream of the lacZ promoter of a pGEM-PlacZ plasmid, thereby constructing pGEM-PlacZaldB-pdc. The constructed pGEM-PlacZ-aldB-pdc was digested with EcoRI-PstI, and then inserted into pBR322, thereby constructing pBR322-PlacZ-aldB-pdc. The constructed plasmid was introduced into the cuΔldhAΔals strain by electroporation to thereby construct the transformed recombinant strain Δ(ldhA als)/pPdc-AldB (FIG. 4 and Table 3).

Pyruvate decarboxylase (Pdc) and aldehyde dehydrogenase (AldB), which promote pyruvate-to-ethanol conversion, were introduced into the mutant Δ(ldhA als) lacking the 2,3-butanediol synthetic pathway, thereby constructing a mutant microbial strain (FIG. 4 and Table 3).

Specifically, a plasmid overexpressing decarboxylase (Pdc) gene and aldehyde dehydrogenase (AldB) gene, which promote pyruvate-to-ethanol conversion, were introduced by electroporation into the mutant Δ(ldhA als) lacking the 2,3-butanediol synthetic pathway, thereby constructing the recombinant strain Δ(ldhA als)/pPdc-AldB. The activities of Pdc and AldB enzymes in the mutant Δ(ldhA als)/pPdc-AldB were examined, and as a result, it was shown that the activities of the enzymes increased (FIG. 5).

TABLE 3

Primer sequences used in construction of pPdc-AldB

| Primer | | Sequence |
|---|---|---|
| pdc | SEQ ID NO. 5 | F:5'-*AGATCT*atggcttcttcaactttttatattcc-3' |
| | SEQ ID NO. 6 | R:5'-*CTCGAG*TCTAGAttagaaagcgctcaggaagagtt-3' |
| aldB | SEQ ID NO. 7 | F:5'-*TCTAGA*atgagttatactgtcggtacctatttagc-3' |
| | SEQ ID NO. 8 | R:5'-*CTCGAG*CTGCAGctagaggagcttgttaacaggcttac-3' |

The glycerol fermentation characteristics of the mutant Δ(ldhA als)/pPdc-AldB were analyzed, and as a result, it was shown that the production of ethanol greatly increased due to increases in the activities of the Pdc and AldB enzymes (Table 1) and that glycerol metabolism and cell growth were restored to levels similar to those in the mutant ΔldhA (FIG. 3). In addition, the production of 1,3-propandiol also increased to a level similar to that in the mutant ΔldhA, but the production of 2,3-butanediol was not substantially observed, like the case of the mutant Δ(ldhA als) (Table 1).

Example 3

Fed-Batch Culture of Klebsiella pneumoniae Mutant Δ(ldhA als)/pPdc-AldB

For fed-batch culture, a 5-L fermenter was used, and the medium used was the same as used in the above-described flask culture, except that it contained 20 mM phosphate buffer (3.4 g/L $K_2HPO_4$ and 1.3 g/L $KH_2PO_4$). Pre-culture was performed in a 1-L flask using 100 mM germ medium at 37° C. and 200 rpm for 10-12 hours. The effective volume of the fermenter was 2 L, and 200 ml of the pre-culture was inoculated.

In the 5-L fermenter containing the medium, fed-batch culture of the mutant Δ(ldhA als)/pPdc-AldB was performed under the conditions of temperature of 37° C., agitation speed of 200 rpm, pH of 6.5 and air feed rate of 2.0 vvm (FIG. 6).

As shown in Table 4 below, the production of 1,3-propanediol in the mutant Δ(ldhA als)/pPdc-AldB was almost similar to that in the mutant ΔldhA, but the production of 2,3-butanediol was lower than that in the mutant Δ(ldhA als), and thus the concentration of 2,3-butanediol relative to 1,3-propanediol in the mutant Δ(ldhA als)/pPdc-AldB was the lowest (14% (mol/mol)).

TABLE 4

Fed-batch culture for glycerol fermentation in *Klebsiella pneumoniae* mutants

|  | ΔldhA (2.0 vvm) | Δ(ldhA als) (2.0 vvm) | Δ(ldhA als)/ pPdc-AldB (2.0 vvm) |
|---|---|---|---|
| 1,3-Propanediol (g/l) | 65.9 | 48.0 | 63.3 |
| 2,3-Butanediol (g/l) | 23.8 | 13.7 | 10.5 |
| Lactate (g/l) | 0 | 0 | 0 |
| Succinate (g/l) | 9.2 | 7.6 | 13.6 |
| Acetate (g/l) | 6.1 | 9.0 | 8.2 |
| Ethanol (g/l) | 5.0 | 5.9 | 15.0 |
| 1,3-Propanediol yield (mol/mol) | 0.57 | 0.71 | 0.51 |
| 2,3-Butanediol/ 1,3-Propanediol (mol/mol) | 0.30 | 0.24 | 0.14 |
| 1,3-Propanediol productivity (g/L/h) | 1.37 | 1.00 | 1.32 |

As shown in FIG. 7, the concentration of pyruvate during growth of the mutant Δ(ldhA als) greatly increased, but the concentration of pyruvate in the mutant Δ(ldhA als)/pPdc-AldB decreased to a level similar to that in the mutant ΔldhA.

Example 4

Figure 8:
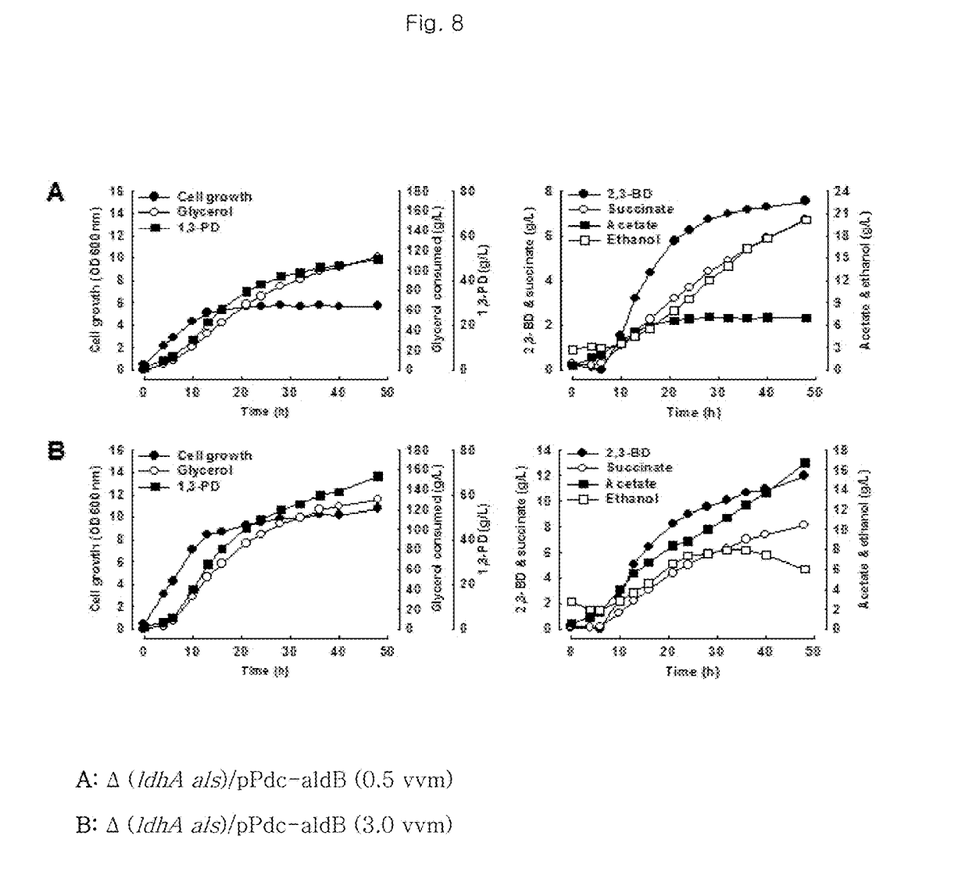
FIG. 8 shows the results of examining the effect of oxygen concentration in a fed-batch culture process for glycerol fermentation in the *Klebsiella pneumoniae* mutant Δ(ldhA als)/pPdc-AldB.

Effect of Oxygen Concentration on Fermentative Metabolism of Glycerol in *Klebsiella pneumoniae* Mutant Δ(ldhA als)/pPdc-aldB In order to examine the effect of oxygen concentration in a fermenter during culture of the mutant Δ(ldhA als)/pPdc-AldB, the fermentative metabolism characteristics of glycerol were analyzed at varying oxygen feed rates of 0.5 and 3.0 vvm while maintaining other conditions at the same levels (FIG. 8). When the amount of air injected into the fermenter was increased from 2.0 vvm to 3.0 vvm, the production of 1,3-propanediol increased from 63.3 g/L to 68.2 g/L, and the production yield and productivity of 1,3-propanediol also increased from 0.51% to 0.63% and from 1.31 g/L/h to 1.42 g/L/h, respectively. However, the production of 2,3-propanediol also increased from 10.5 g/L to 12.0 g/L, and thus the ratio of 2,3-butanediol to 1,3-propanediol was maintained at a similar level. On the other hand, when the amount of air injected into the fermenter was reduced to 0.5 vvm, the production of 1,3-propanediol greatly decreased (Table 5).

TABLE 5

Effect of amount of air injected into fermenter in fed-batch culture of mutant Δ(ldhA als)/pPdc-AldB.

| | Δ(ldhA als)/pPdc-AldB | |
|---|---|---|
| | Low (0.5 vvm) | High (3.0 vvm) |
| 1,3-Propanediol (g/l) | 49.4 (63.3) | 68.2 |
| 2,3-Butanediol (g/l) | 7.6 (10.5) | 12.0 |
| Lactate (g/l) | 0 | 0 |
| Succinate (g/l) | 6.7 (13.6) | 8.1 |
| Acetate (g/l) | 7.0 (8.2) | 16.7 |
| Ethanol(g/l) | 20.2 (15) | 8.0 |
| 1,3-Propanediol yield (mol/mol) | 0.52 (0.51) | 0.63 |
| 2,3-Butanediol/ 1,3-Propanediol (mol/mol) | 0.13 (0.14) | 0.15 |
| 1,3-Propanediol productivity (g/L/h) | 1.03 (1.32) | 1.42 |

INDUSTRIAL APPLICABILITY

The use of the glycerol-fermenting mutant microorganism according to the present invention can significantly increase the production of 1,3-propanediol while minimizing the production of 2,3-butanediol.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A mutant microorganism wherein a gene encoding lactate dehydrogenase and a gene encoding an enzyme which is involved in 2,3-butanediol synthesis are deleted in a microorganism having the ability to produce 1,3-propanediol from glycerol and wherein a gene encoding pyruvate decarboxylase and a gene encoding aldehyde dehydrogenase are introduced or amplified.

2. The mutant microorganism of claim 1, wherein the enzyme which is involved in 2,3-butanediol synthesis is an acetolactate synthase.

3. The mutant microorganism of claim 1, wherein the gene encoding pyruvate decarboxylase is pdc derived from a strain, which has pyruvate decarboxylase activity.

4. The mutant microorganism of claim 1, wherein the gene encoding aldehyde dehydrogenase is aldB derived from a strain, which has pyruvate decarboxylase activity.

5. The mutant microorganism of claim 1, which is *Klebsiella pneumonia*.

6. A method for producing 1,3-propanediol, comprising the steps of:
   (a) culturing the mutant microorganism of claim 1 in a glycerol-containing medium to produce 1,3-propanediol; and
   (b) recovering the produced 1,3-propanediol.

7. The method of claim 6, wherein an air injection amount for the culturing of step (a) is 2.0~5.0 vvm.

* * * * *

UNITED STATES PATENT AND TRADEMARK OFFICE
CERTIFICATE OF CORRECTION

PATENT NO. : 9,896,701 B2
APPLICATION NO. : 15/120516
DATED : February 20, 2018
INVENTOR(S) : Chul Ho Kim Page 1 of 1

It is certified that error appears in the above-identified patent and that said Letters Patent is hereby corrected as shown below:

In the Specification

Column 5, Line 44: "by" should be -- bp --

Column 5, Line 61: "by" should be -- bp --

Column 6, Line 13: "Mg504" should be -- MgSO4 --

Column 6, Line 13: "CaCl2.2H2O" should be -- CaCl2•2H2O --

Column 6, Line 14: "FeSO4.7H2O" should be -- FeSO4•7H2O --

Column 6, Line 16: "MnCl2.4H2O" should be -- MnCl2•4H2O --

Column 6, Line 17: "CoCl2.4H2O" should be -- CoCl2•4H2O --

Column 6, Line 17: "CuCl2.2H2O" should be -- CuCl2•2H2O --

Column 6, Line 18: "NiCl2.6H2O" should be -- NiCl2•6H2O --

Column 6, Line 18: "Na2MoO4.2H2O" should be -- Na2MoO4•2H2O --

Signed and Sealed this
Twenty-sixth Day of June, 2018

Andrei Iancu
*Director of the United States Patent and Trademark Office*